US008675820B2

(12) United States Patent
Baic et al.

(10) Patent No.: US 8,675,820 B2
(45) Date of Patent: Mar. 18, 2014

(54) ELECTRONIC CONICAL COLLIMATOR VERIFICATION

(75) Inventors: Dusan Baic, Palo Alto, CA (US); Kevin Greenberg, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 596 days.

(21) Appl. No.: 12/854,045

(22) Filed: Aug. 10, 2010

(65) Prior Publication Data

US 2012/0039444 A1     Feb. 16, 2012

(51) Int. Cl.
*H05G 1/56*        (2006.01)
*G21K 1/02*        (2006.01)

(52) U.S. Cl.
USPC .......................................... 378/148; 378/114

(58) Field of Classification Search
USPC ......... 378/113, 114, 147, 148, 156, 157, 160, 378/205, 210
See application file for complete search history.

(56) References Cited

U.S. PATENT DOCUMENTS

| | | | | |
|---|---|---|---|---|
| 3,982,133 | A * | 9/1976 | Jupa et al. ....................... | 378/148 |
| 4,172,979 | A * | 10/1979 | Morrison ......................... | 378/65 |
| 4,359,642 | A * | 11/1982 | Heinz et al. .................... | 378/150 |
| 5,396,889 | A * | 3/1995 | Ueda et al. ...................... | 600/407 |
| 5,519,223 | A * | 5/1996 | Hug et al. ................... | 250/363.1 |
| 5,945,684 | A * | 8/1999 | Lam et al. .................... | 250/492.3 |
| 6,590,214 | B1 * | 7/2003 | Karmalawy ................ | 250/363.1 |
| 6,888,919 | B2 | 5/2005 | Graf | |
| 7,649,981 | B2 | 1/2010 | Seppi et al. | |
| 2003/0230723 | A1 * | 12/2003 | Garrard et al. ............. | 250/363.1 |
| 2008/0107239 | A1 * | 5/2008 | Sayeh et al. ................... | 378/148 |
| 2012/0039444 | A1 * | 2/2012 | Baic et al. ...................... | 378/147 |

FOREIGN PATENT DOCUMENTS

JP        57072087 A   *   5/1982      .............. G01T 1/164

* cited by examiner

*Primary Examiner* — Thomas R Artman
(74) *Attorney, Agent, or Firm* — Vista IP Law Group, LLP

(57) ABSTRACT

A device for use with a radiation machine includes a first cone collimator, wherein the first cone collimator has a first end for receiving a radiation beam, a collimating portion for changing the radiation beam, and a second end for emitting an output beam, and wherein the first cone collimator is configured to be detachably coupled to a coupling device that has a plurality of moveable switches, and has one or more engaging portions configured to engage with a first subset of the plurality of switches. A method of using a cone collimator includes receiving a portion of a cone collimator, determining a subset of a plurality of switches that is pressed by the cone collimator, and determining an identity of the cone collimator based on the subset of the plurality of switches that is pressed by the cone collimator.

28 Claims, 17 Drawing Sheets

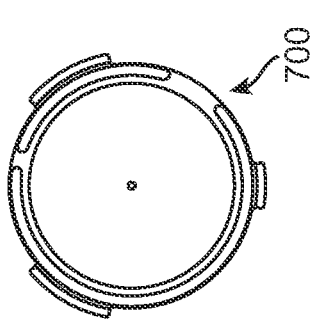
FIG. 11
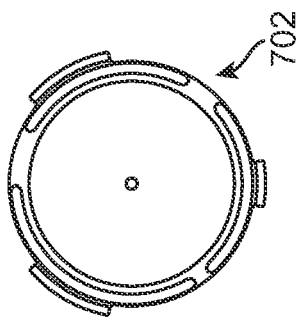
FIG. 12
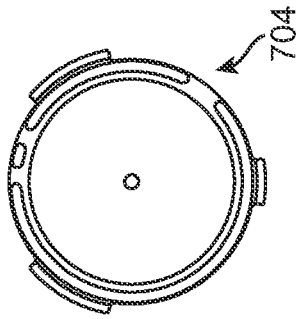
FIG. 13
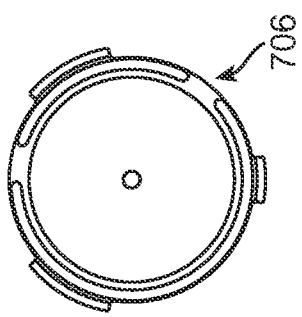
FIG. 14
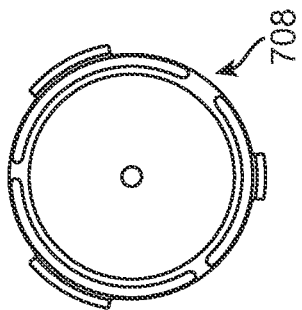
FIG. 15
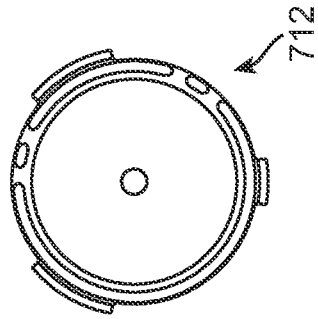
FIG. 16
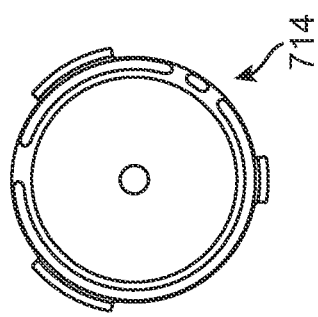
FIG. 17
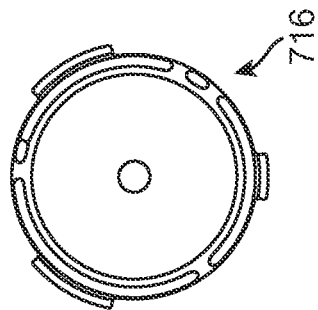
FIG. 18
FIG. 19

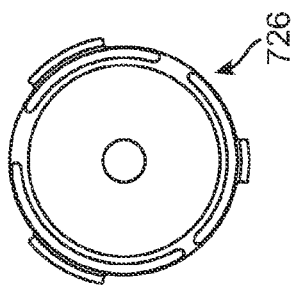
FIG. 20 · FIG. 21 · FIG. 22 · FIG. 23 · FIG. 24
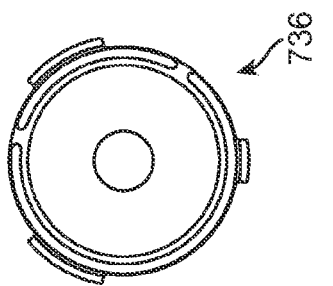
FIG. 25 · FIG. 26 · FIG. 27 · FIG. 28 · FIG. 29

ELECTRONIC CONICAL COLLIMATOR VERIFICATION

FIELD

This application relates generally to radiation treatment systems and methods, and more specifically, to radiation treatment systems and methods that involve a conical collimator.

BACKGROUND

Radiation therapy has been employed to treat tumorous tissue. In radiation therapy, a high energy beam is applied from an external radiation source towards the patient. The external radiation source, which may be rotating (as in the case for arc therapy), produces a beam of radiation that is directed into the patient to the target site. The dose and placement of the dose must be accurately controlled to ensure that the tumor receives sufficient radiation, and that damage to the surrounding healthy tissue is minimized.

In certain treatment procedures, such as a procedure for treating a brain tumor, it may be desirable to produce a treatment radiation beam having a small profile (e.g., cross sectional dimension), thereby allowing precise treatment of the targeted tissue. In such treatment procedure, a conical collimator may be employed to change a cone beam provided by the radiation source into a pencil beam with a certain desired cross sectional dimension. The pencil beam allows targeted tissue to be precisely irradiated. In some cases, different conical collimators with different configurations may be provided for producing pencil beams with different respective cross sectional dimensions. During use, the operator of the radiation machine chooses one of the available conical collimators for use with the radiation machine, depending on the particular size of the pencil beam required by a treatment plan.

In existing techniques, the operator may be required to manually check the conical collimator to make sure that the particular conical collimator being used with the radiation machine is the proper size. However, Applicants of the subject application determines that manually checking the conical collimator is inconvenient and may not be reliable as such technique may be subject to human error. Thus, applicants of the subject application determine that it would be desirable to provide a new device and method for conical collimator verification.

SUMMARY

In accordance with some embodiments, a device for use with a radiation machine includes a structure for mounting to the radiation machine, a coupling device coupled to the structure, the coupling device having an opening for accommodating a portion of a first cone collimator, and a plurality of moveable switches at the coupling device, wherein one or more of the plurality of switches are configured to be actuated in response to the portion of the first cone collimator being placed in the opening.

In accordance with other embodiments, a device for use with a radiation machine includes a first cone collimator, wherein the first cone collimator has a first end for receiving a radiation beam, a collimating portion for changing the radiation beam, and a second end for emitting an output beam, and wherein the first cone collimator is configured to be detachably coupled to a coupling device that has a plurality of moveable switches, and has one or more engaging portions configured to engage with a first subset of the plurality of switches.

In accordance with other embodiments, a method of using a cone collimator includes receiving a portion of a cone collimator, determining a subset of a plurality of switches that is pressed by the cone collimator, and determining an identity of the cone collimator based on the subset of the plurality of switches that is pressed by the cone collimator.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIGS. 11-69 illustrates conical collimators with different respective configurations in different embodiments.

DESCRIPTION OF THE EMBODIMENTS

Figure 1:
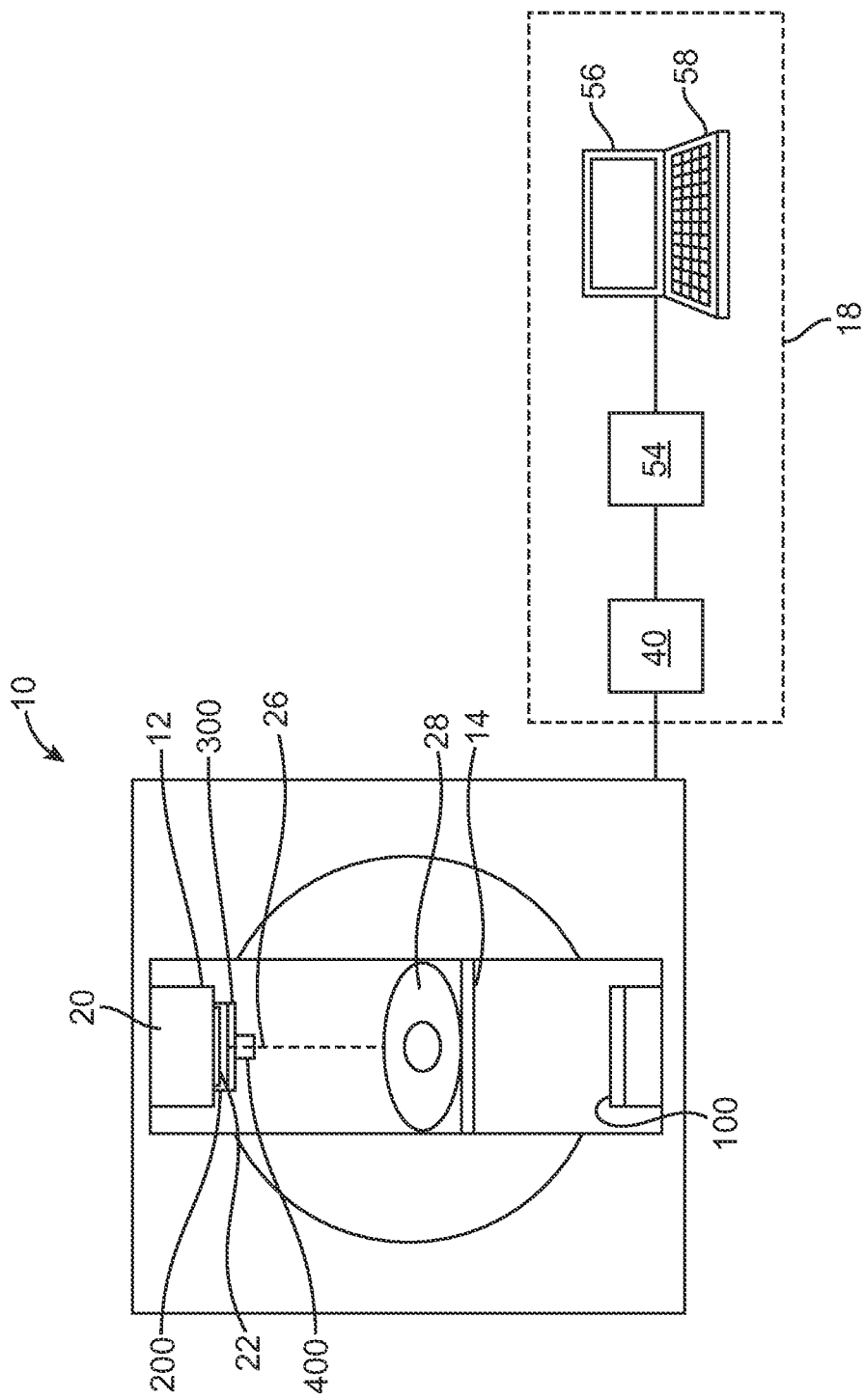
FIG. 1 illustrates a system for delivering radiation in accordance with embodiments described herein.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a radiation treatment system 10 for delivering radiation in accordance with a treatment plan that is determined using techniques described herein. The system 10 includes a gantry 12 (in the form of an arm), a patient support 14 for supporting a patient, and a control system 18 for controlling an operation of the gantry 12. The system 10 also includes a radiation source 20 for providing a radiation beam, and a collimator 22 for shaping the radiation beam. In some cases, the collimator 22 may be considered to be a component of the radiation source 20. By means of non-limiting examples, the collimator 22 may include one or more blocks, or may include a plurality of leaves for blocking at least some of the radiation generated by the radiation source 20. Also, the gantry 12, the source 20, and the collimator 22 may be considered to be parts of the radiation machine 10. In the illustrated embodiments, the radiation source 20 is configured to generate a cone beam. In other embodiments, the radiation source 20 may be configured to generate a fan beam, or other types of radiation beams.

In the illustrated embodiments, a mounting device 300 is provided for detachably coupling a conical collimator 400 to an interface structure 200 at the radiation machine 10. The conical collimator 400 is configured to receive a cone shape radiation beam emitted by the source 20 and through the collimator 22, change the configuration of the beam from a cone shape to a pencil shape, and output the pencil shape radiation beam. The mounting device 300 includes components for generating signals for determining whether the conical collimator 400 is desirably positioned relative to the mounting device 300, for determining whether the conical collimator 400 has been locked in position, and for determining an identification of the conical collimator 400. The interface structure 200, the mounting device 300, and the conical collimator 400 will be described in further details.

In the illustrated embodiments, the radiation source 20 is a treatment radiation source for providing treatment energy. In other embodiments, in addition to being a treatment radiation source, the radiation source 20 can also be a diagnostic radiation source for providing diagnostic energy. In such cases, the system 10 will include an imager, such as the imager 100, located at an operative position relative to the source 20 (e.g., under the support 14). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003. In the illustrated embodiments, the radiation source 20 is coupled to the arm gantry 12. Alternatively, the radiation source 20 may be located within a bore.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during a treatment procedure, the gantry 12 rotates about the patient 16 (as in an arc-therapy). In other embodiments, the gantry 12 does not rotate about the patient 16 during a treatment procedure. In such case, the gantry 12 may be fixed, and the patient support 14 is rotatable. The operation of the radiation source 20, the collimator system 22, and the gantry 12 (if the gantry 12 is rotatable), are controlled by the control 40, which provides power and timing signals to the radiation source 20 and the collimator system 22, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

It should be noted that the system 10 is not limited to the configuration described above, and that the system 10 may have other configurations in other embodiments. For example, in other embodiments, the system 10 may have a different shape, such as a structure with an opening or a through bore. In other embodiments, the radiation source 20 of the system 10 may have different ranges of motions and/or degrees of freedom. For example, in other embodiments, the radiation source 20 may be rotatable about the patient 28 completely through a 360° range, or partially through a range that is less than 360°. Also, in other embodiments, the radiation source 20 is translatable relative to the patient 28. Further, the radiation source 20 is not limited to delivering treatment energy in the form of x-ray, and may deliver other types of radiation energy. For example, in other embodiments, the radiation source 20 may be a proton source for delivering protons to treat patient, or other types of particle source for delivering other types of particles for treating patient.

Figure 2:
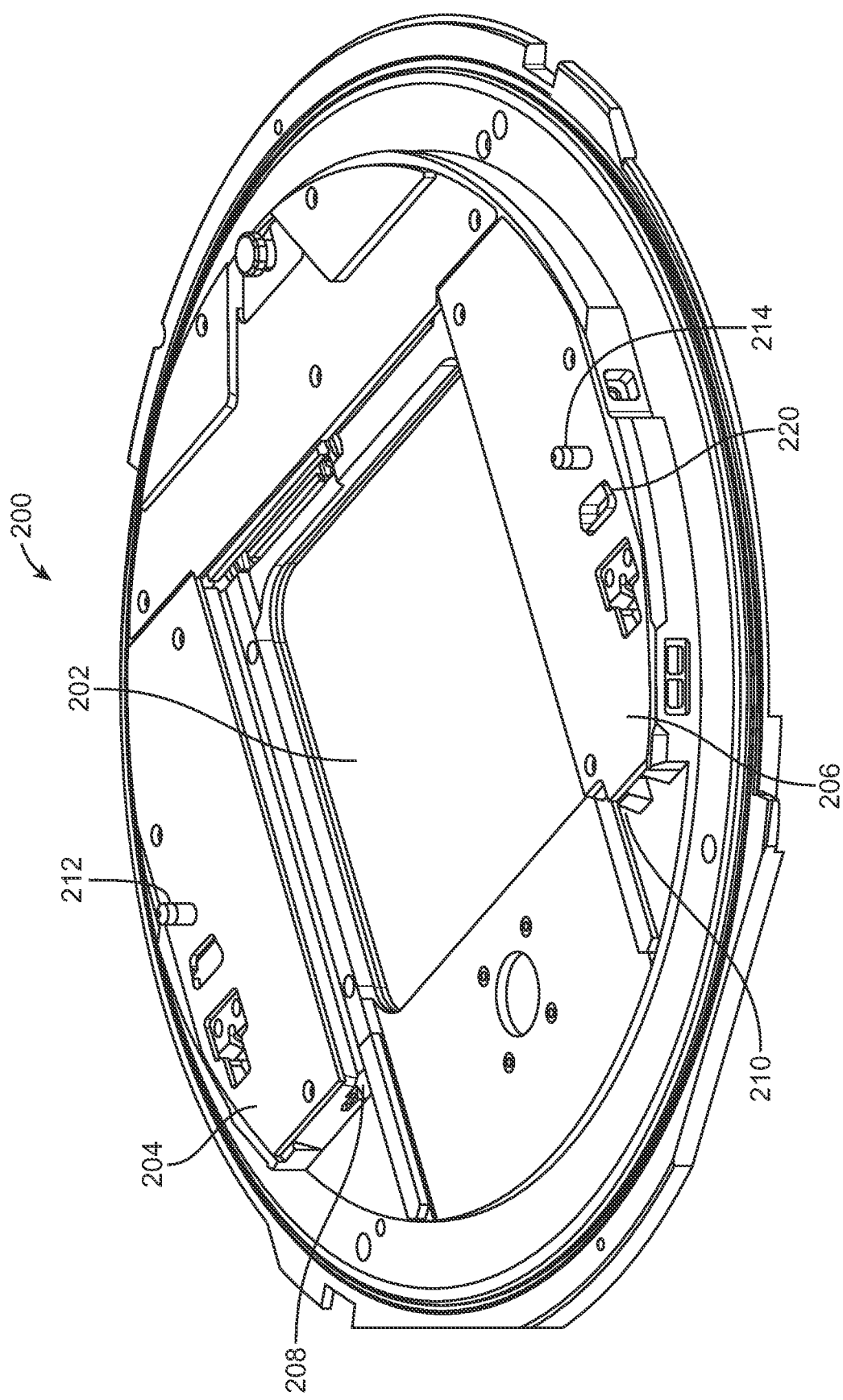
FIG. 2 illustrates an interface structure of the radiation system of FIG. 1.

FIG. 2 illustrates the interface structure 200 that is a part of the radiation machine 10 in accordance with some embodiments. As used in this specification, the term "interface structure" may be any part or parts of the radiation machine to which a conical collimator may be coupled, either directly or indirectly. The interface structure 200 includes an opening 202 for allowing radiation to exit therethrough after the radiation has been collimated by the collimator 22. The interface structure 200 also includes a first portion 204 and a second portion 206 defining a first slot 208 and a second slot 210, respectively. As shown in the figure, the first portion 204 and the second portion 206 are on opposite sides of the opening 202. The interface structure 200 also includes a first pin 212, a second pin 214, and an electrical connector 220 for engagement with different respective components of the mounting device 300. The electrical connector 220 is electrically connected to the processor 54 (or another processor) for processing information received from the mounting device 300.

Figure 3:
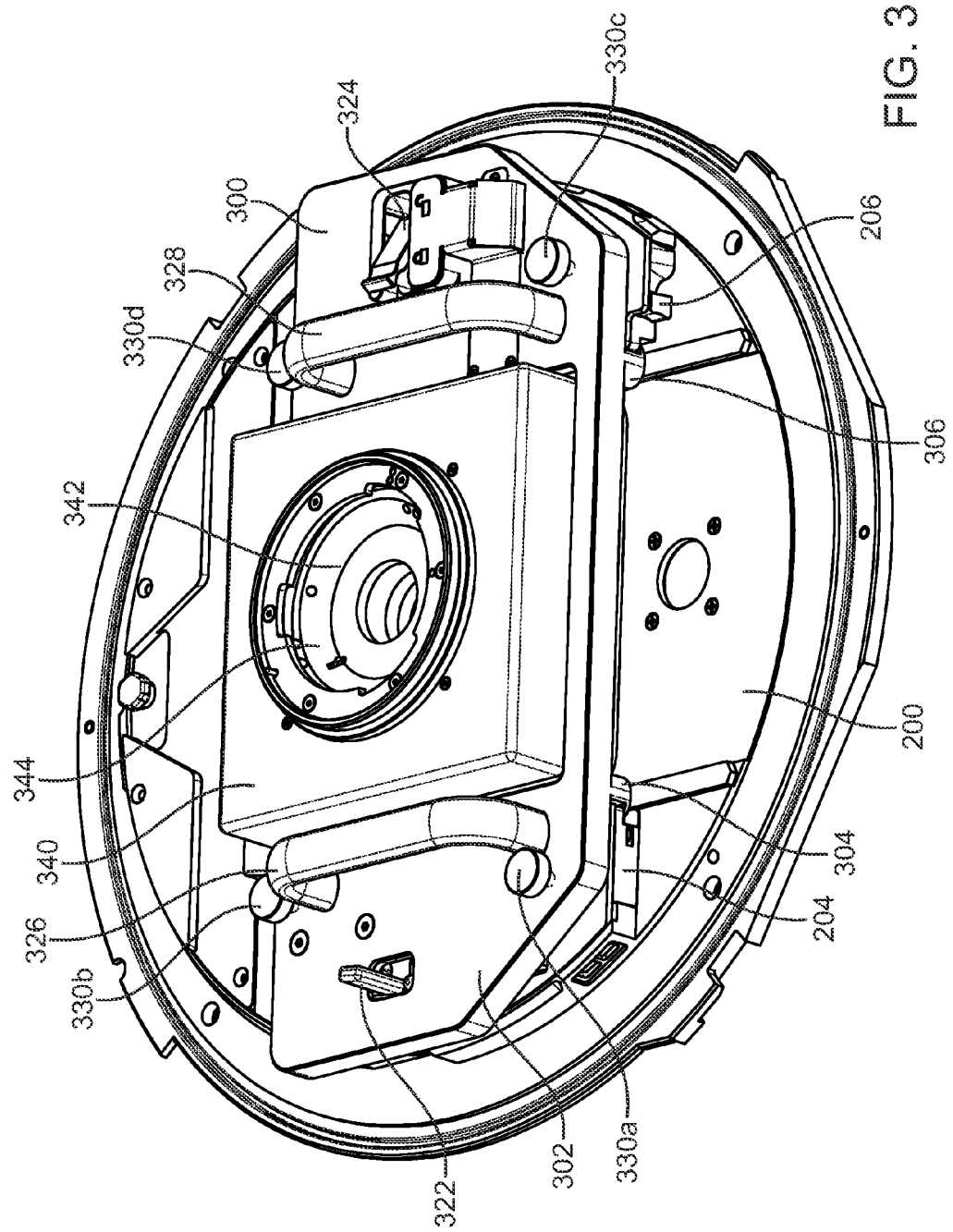
FIG. 3 illustrates a mounting device being mounted to the radiation system of FIG. 1 in accordance with some embodiments.
Figure 4:
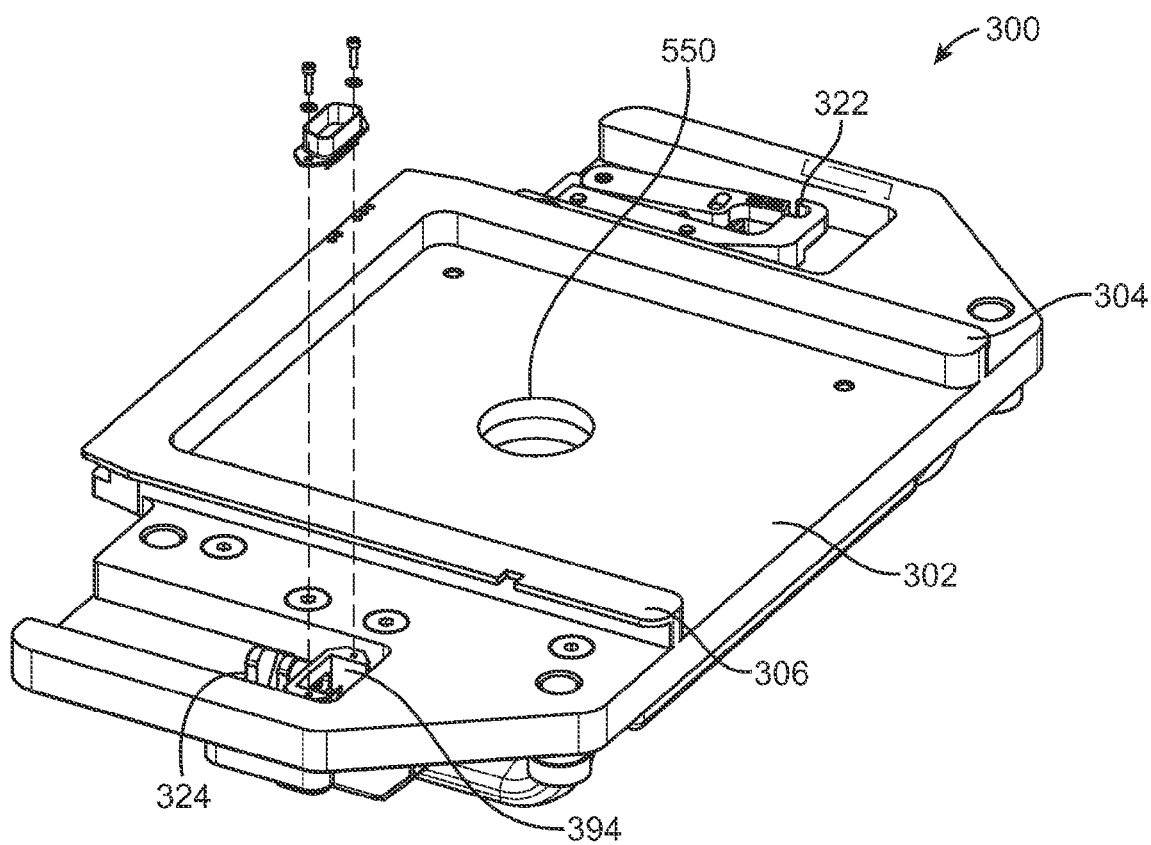
FIG. 4 illustrates an underside of the mounting device of FIG. 3 in accordance with some embodiments.

FIG. 3 illustrates the mounting device 300 being mounted to the interface structure 200 of the radiation machine. The underside of the mounting device 300 that faces against the interface structure 200 is shown in FIG. 4. The mounting device 300 includes a support structure 302, and portions 304, 306 configured (sized and/or shaped) for slidably engagement with the respective first and second slots 208, 210. The mounting device 300 includes handles 326, 328 for allowing a user to carry the mounting device 300. During use, the user holds onto the handles 326, 328, and places the mounting device 300 into an operative position relative to the interface structure 200 by sliding the portions 304, 306 into the respective slots 208, 210. The mounting device 300 also includes a first securing mechanism 322 and a second securing mechanism 324 for engagement with the respective first and second pins 212, 214 at the interface structure 200. When the mounting device 300 has been slid into the operative position, the securing mechanisms 322, 324 lock against the pins 212, 214, thereby preventing the mounting device 300 from moving relative to the interface structure 200 during use.

The mounting device 300 also includes four thumb screws 330a-330d, which are placed through four respective openings at the mounting device 300 and are anchored against four corresponding openings at the interface structure 200. The thumb screws 330a-330d further secure the mounting device 300 relative to the interface structure 200, and prevent the mounting device 300 from sliding off from the interface structure 200. In some embodiments, each of the thumb screws 330a-330d has a small brass pad that will press on the interface structure 200. This will provide additional secure locking by friction in the axial direction (in the direction along the length of the thumb screw).

In the illustrated embodiments, the securing mechanism 322 includes a latch that is spring loaded, which requires manual actuation to unlatch. The securing mechanism 324 also includes a latch that is actuated manually, and is configured to drive the electrical connector 394 to connect to the electrical connector 220 at the interface structure 200. In particular, actuating the latch of the securing mechanism 324 will cause the mounting device 300 to lock against the pin at the interface structure 200, and move the electrical connector 394 to engage with the electrical connector 220 to thereby form an electrical connection. The securing mechanisms 322, 324 allow the mounting device 300 to be repeatedly and automatically placed at a desired position relative to the interface structure 200 when the securing mechanisms 322, 324 are locked against the pins 212, 214.

The mounting device 300 also includes a coupling device 340 that is moveably coupled to the support structure 302. As used in this specification, the term "coupling device" may refer to any device(s) or component(s) that is configured to couple to the conical collimator 400, either directly or indirectly. The coupling device 340 includes an opening 342 for accommodating a portion of a conical collimator, and an interface device 344 for interfacing with the conical collimator 400. In the illustrated embodiments, the interface device 344 has a conical seat configuration for corresponding with at least a portion of the collimator 400. In other embodiments, the interface device 344 may have other configurations as long as it can interface or correspond with the collimator 400.

In some embodiments, the mounting device 300 may further include its own code (e.g., in the form of machined indentations or openings) that is configured to be read by optical reader at the interface structure 200. In such cases, based on the code sensed by the optical reader, the optical reader then sends a signal to the processor 54 (or another processor) to inform the system 10 that the mounting device 300 is in its operative position relative to the interface structure 200.

Figure 5:
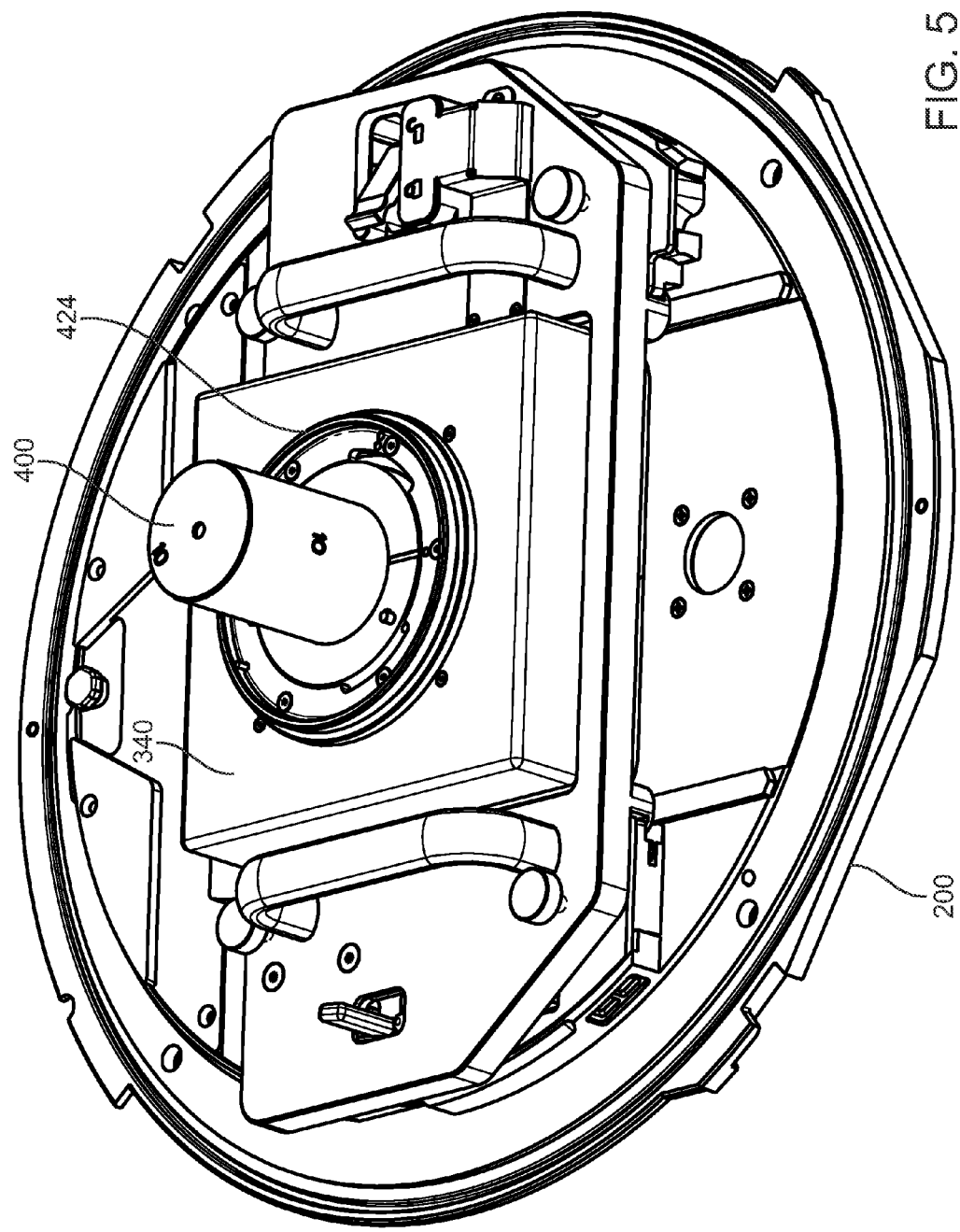
FIG. 5 illustrates a conical collimator being placed into an opening of the mounting device of FIG. 3.
Figure 6:
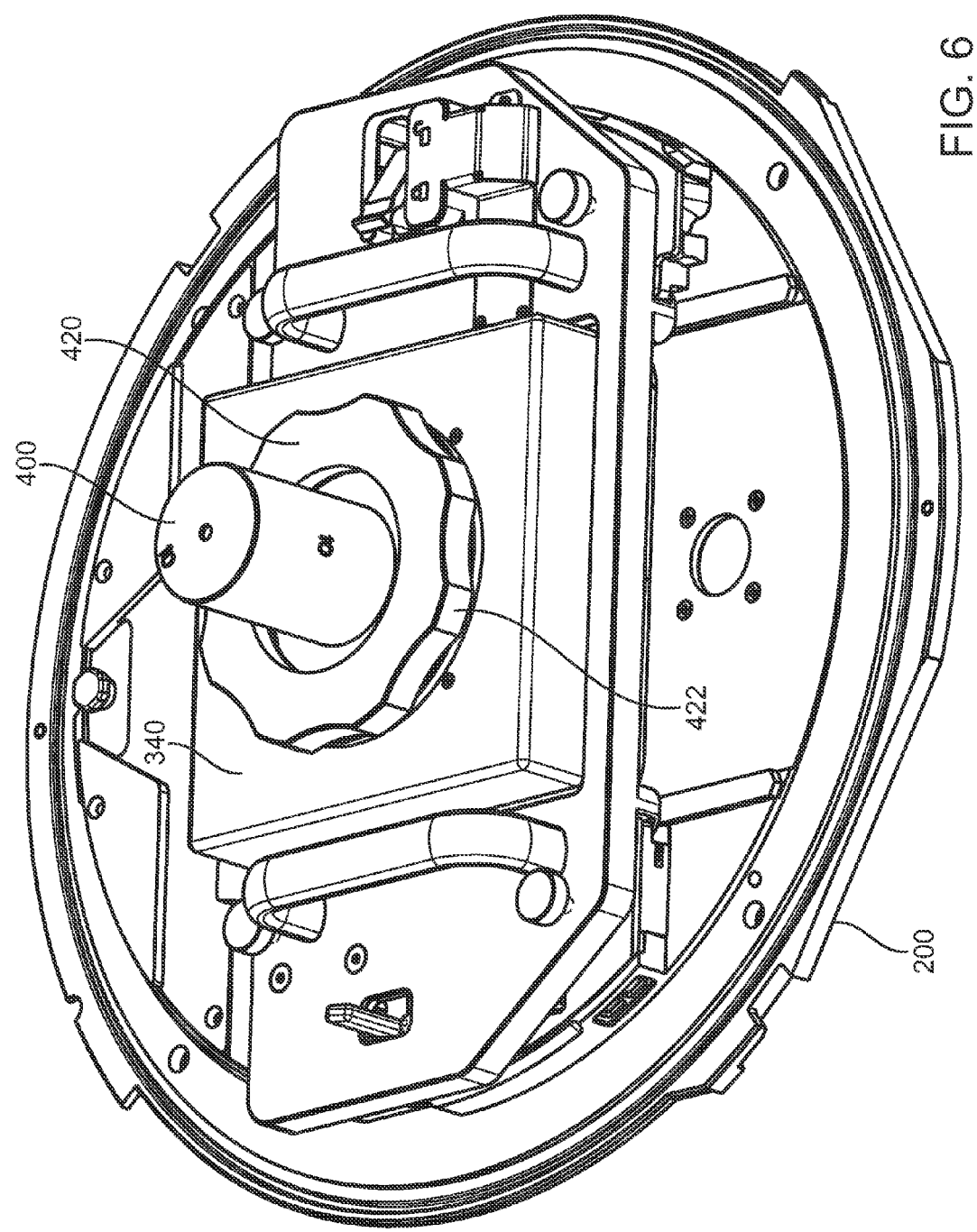
FIG. 6 illustrates a locking ring for pressing the conical collimator against the mounting device and for locking the conical collimator against the mounting device in accordance with some embodiments.

FIG. 5 illustrates the conical collimator 400 being placed into the opening 342 of the coupling device 340, thereby allowing parts of the conical collimator 400 to engage with components at the interface device 344. As shown in FIG. 6, after the conical collimator 400 has been placed into the opening 342 of the coupling device 340, a user may use a locking ring 420 to press the conical collimator 400 towards the interface device 344, and to secure the conical collimator 400 relative to the coupling device 340 so that the conical collimator 400 remains stationary relative to the coupling device 340 during use. In the illustrated embodiments, the locking ring 420 includes a first ring structure 422 with threads that are configured to engage with threads 424 (shown in FIG. 5) at the coupling device 340. The locking ring 420 also includes a second ring structure located concentrically underneath the first ring structure 422. The second ring structure may be coupled to the first ring structure 422 via a spring. During use, when the locking ring 420 is being screwed against the threads 424 at the coupling device 340, the second ring structure engages with a part of the conical collimator 400. As the locking ring 420 is further screwed onto the coupling device 340, the second ring structure compresses against the conical collimator 400 to press the conical collimator 400 against components at the interface device 344 of the coupling device 340. The spring between the first and second ring structures holds the conical collimator 400 in place (in interface device 344) while providing some working range for the switch (button 380) to be safely actuated.

Figure 7:
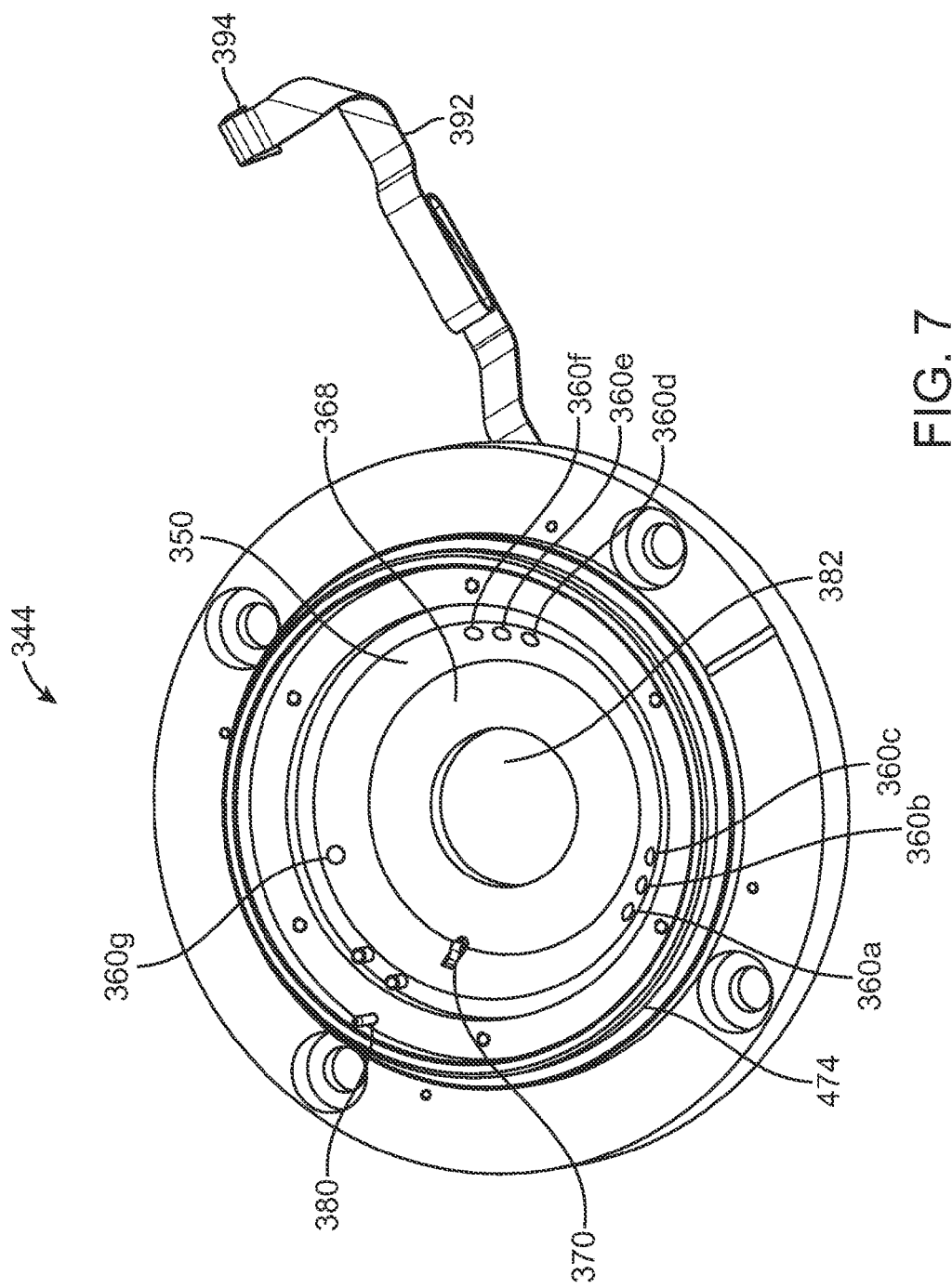
FIG. 7 illustrates an interface device in accordance with some embodiments.
Figure 8:
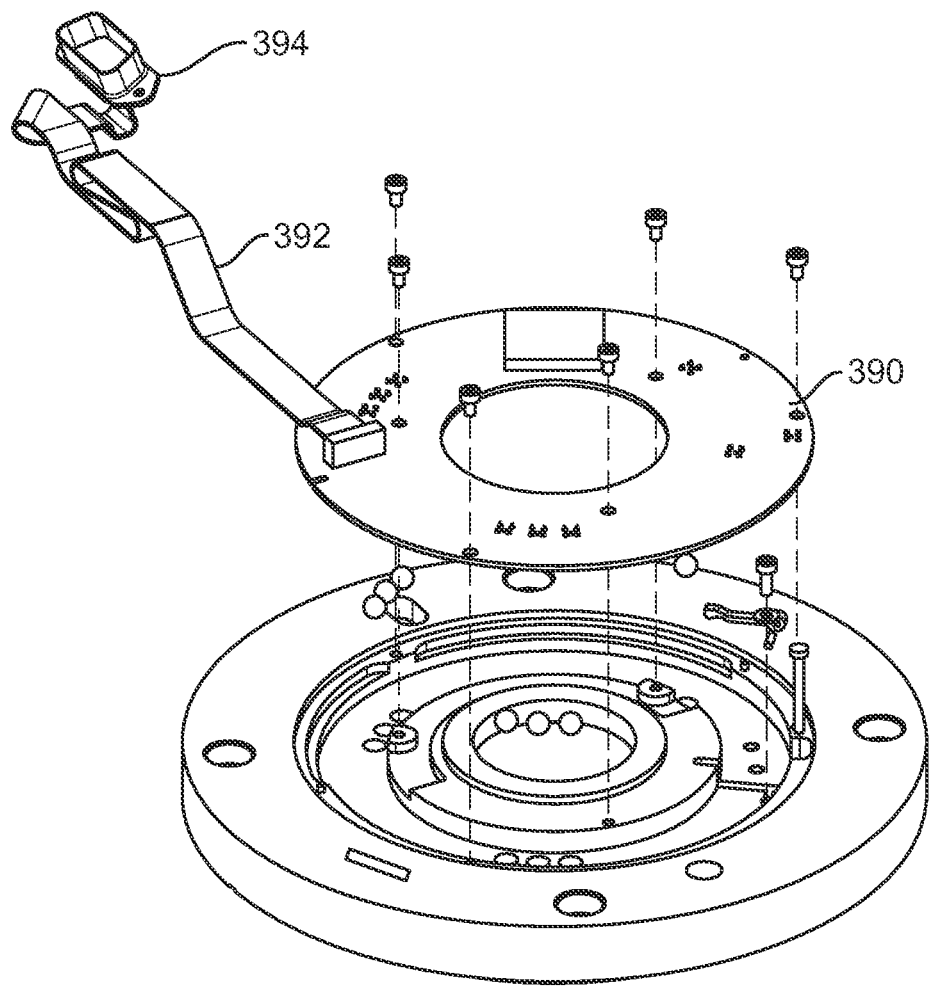
FIG. 8 illustrates a printed circuit board of the interface device of FIG. 7 in accordance with some embodiments.

FIG. 7 illustrates the interface device 344 of the coupling device 340 in accordance with some embodiments. The interface device 344 includes a ring surface 350 and a plurality of switches 360a-360g that are moveable relative to the ring surface 350. In the illustrated embodiments, each of the switches 360 has a curvilinear surface (e.g., a half sphere or a full sphere) that is configured to be engaged by component(s) of the conical collimator 400. In some embodiments, each of the switches 360 may be implemented using a ball switch that is moveable relative to the ring surface 350. The interface device 344 also includes a lever 370 that is configured to be actuated in response to the conical collimator 400 being placed on the surface 368 of the interface device 344 (like that shown in FIG. 5). The interface device 344 further includes a button 380 configured to be actuable in response to the locking ring 420 being placed in its operative position against the interface device 344 (like that shown in FIG. 6). As shown in the figure, the interface device 344 also includes an opening 382 that aligns with the opening 202 at the interface structure 200 of the radiation machine 10 when the mounting device 300 is removably installed onto the radiation machine 10. The opening 202 allows radiation from the radiation source 20 to enter therethrough and be received by the conical collimator 400. As shown in FIG. 8, the interface device 344 also includes a printed circuit board (PCB) 390 attached on the other side of the interface device 344, an electrical cable 392 connected to the PCB 390, and an electrical connector 394 at an end of the cable 392.

Figure 9:
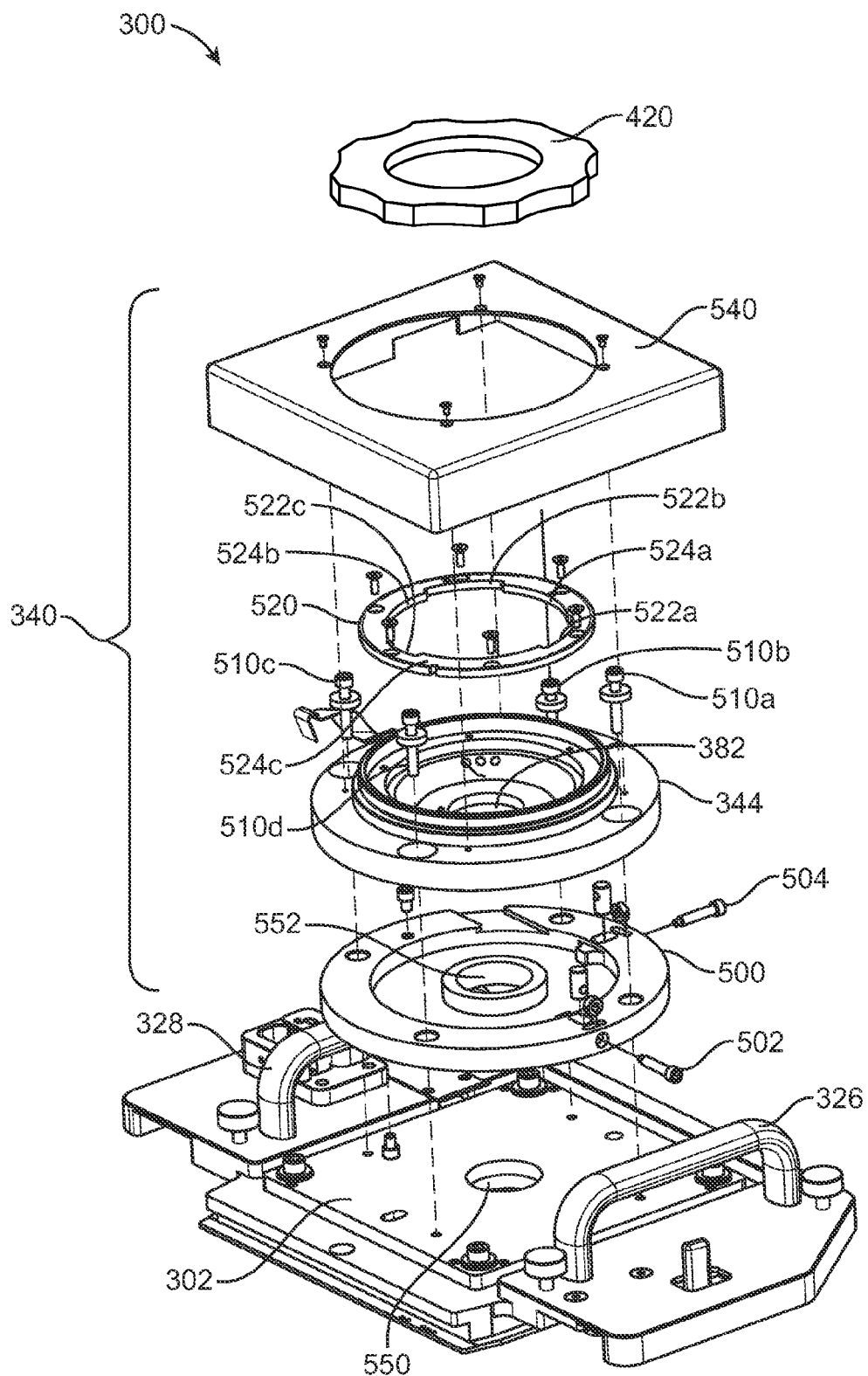
FIG. 9 illustrates an exploded view of the mounting device of FIG. 3 in accordance with some embodiments.

FIG. 9 illustrates an exploded view of the mounting device 300, showing the various components of the mounting device 300 in accordance with some embodiments. As shown in the figure, the coupling device 340 includes the interface device 344 as described previously. The coupling device 340 also includes a base 500 that is moveably coupled to the support structure 302 of the mounting device 300 via two adjustable pins 502, 504. In particular, during use, the pins 502, 504 may be selectively turned to adjust the position of the base 500 relative to the support structure 302 along two respective orthogonal axes. The interface device 344 is secured to the base 500, and is moveably coupled to the support structure 302 by four adjustable pins 510a-510d. During use, the pins 510a-510d may be selectively turned to tilt the interface device 344 about different axes relative to the support structure 302. In one method of use, after the mounting device 300 is removeably mounted to the radiation machine 10, the pins 502, 504 may be used to adjust the position (e.g., X and Y positions) of the interface device 344 relative to the support structure 302, and the pins 510a-510d may be used to adjust the orientation of the interface device 344 relative to the support structure 302. After the position and orientation of the interface device 344 have been desirably adjusted, a cover 540 may then be placed over the interface device 344 to prevent accidental operation of the pins 502, 504, 510a-510d.

As shown in the figure, the interface device 344 also includes a secure ring 520 for allowing the cone collimator 400 to be detachably coupled to the interface device 344. The secure ring 520 has three recesses 522a-522c, and three locking portions 524a-524c next to the three recesses 522a-522c. The recesses 522a-522c are configured to accommodate portions of the conical collimator 400 and allow the portions of the conical collimator 400 to pass therethrough during use. The conical collimator 400 can then be turned so that the portions of the collimator 400 are locked underneath the locking portions 524a-524c of the secure ring 520.

As shown in FIG. 9, the support structure 302 has an opening 550 that aligns with the opening 202 at the interface structure 200 of the radiation machine 10. Also, the base 500 includes an opening 552 that aligns with the opening 550 of the support structure 302 and the opening 382 at the interface device 344. During use, radiation from the radiation machine 10 will exit through the opening 550 at the support structure 302, and will go through the opening 552 and the opening 382 to reach the cone collimator 400.

Figure 10:
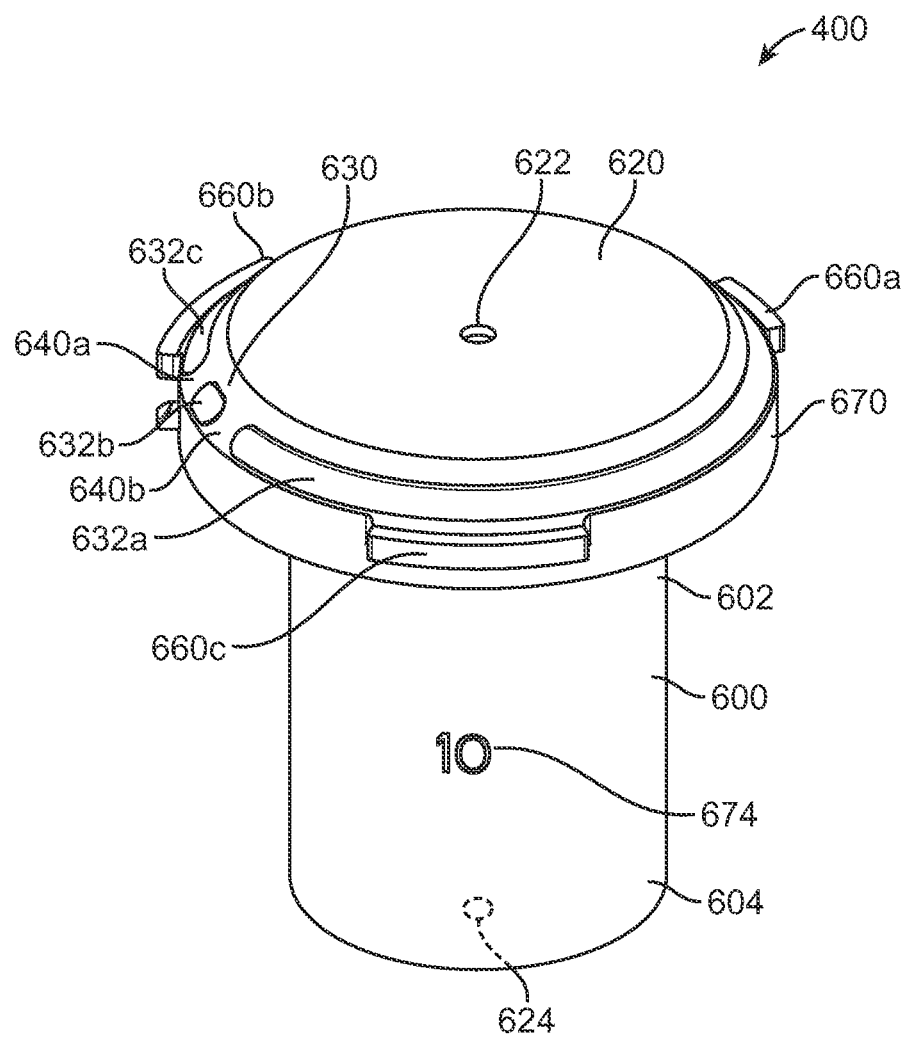
FIG. 10 illustrates a conical collimator that may be used with the mounting device of FIG. 3 in accordance with some embodiments.
Figure 30:
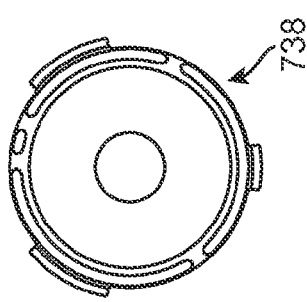
Figure 31:
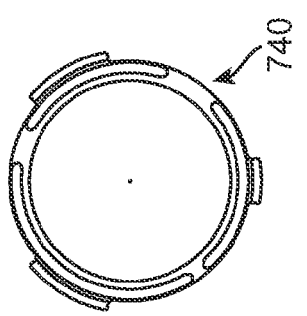
Figure 32:
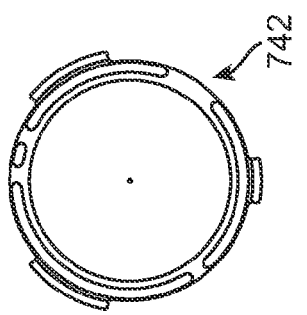
Figure 33:
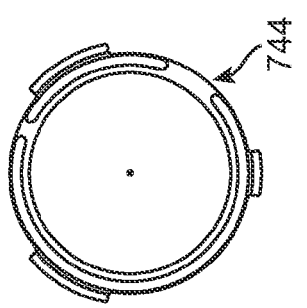
Figure 34:
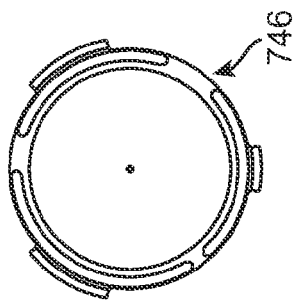
Figure 35:
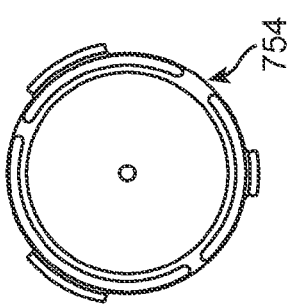
Figure 36:
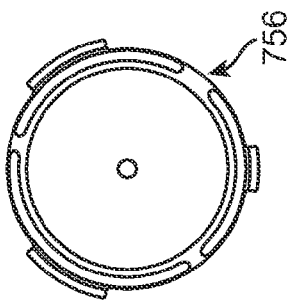
Figure 37:
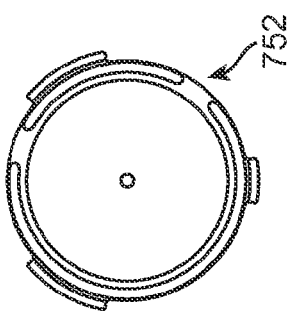
Figure 38:
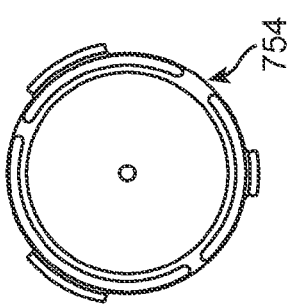
Figure 39:
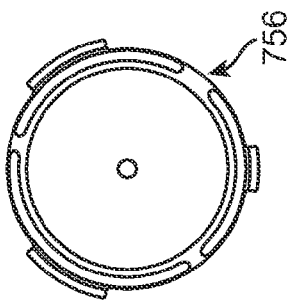
Figures 40, 41, 42, 43, 44:
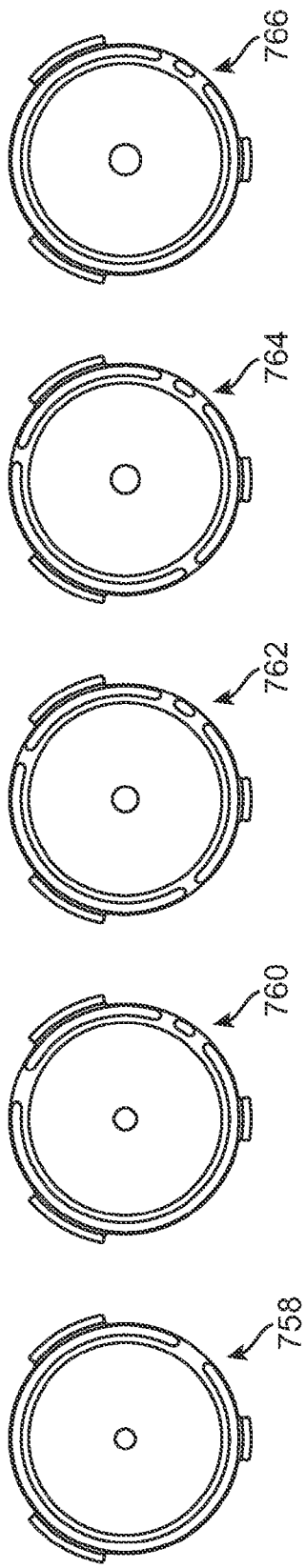
Figures 45, 46, 47, 48, 49:
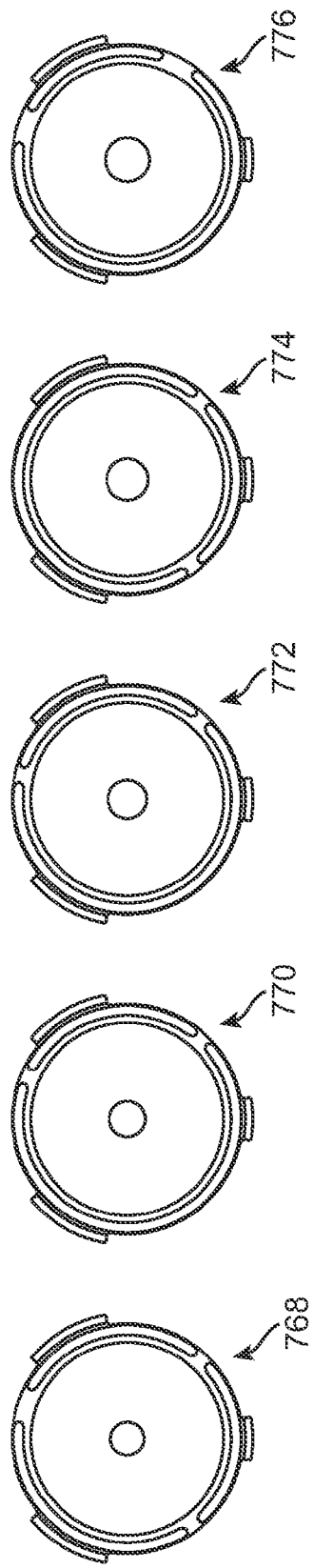
Figure 50:
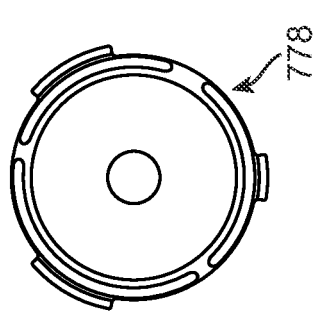
Figure 51:
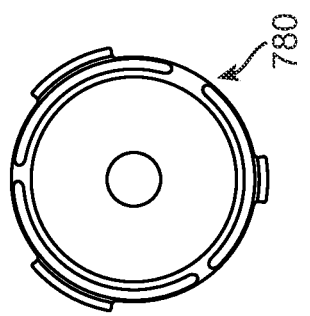
Figure 52:
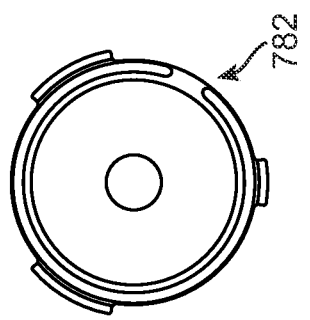
Figure 53:
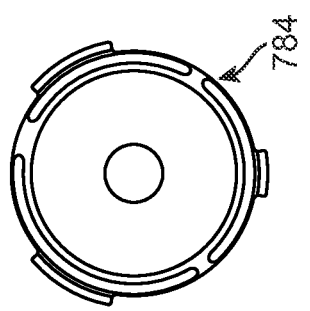
Figure 54:
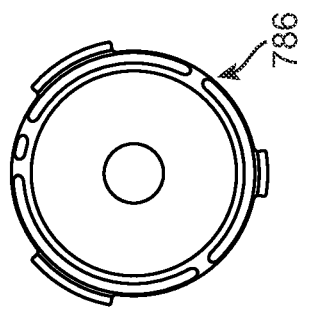
Figure 55:
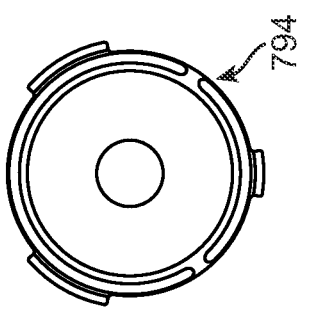
Figure 56:
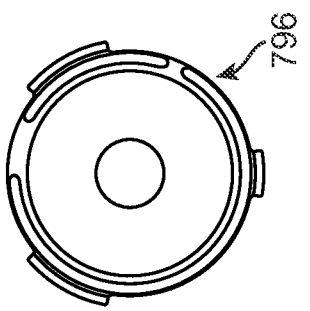
Figure 57:
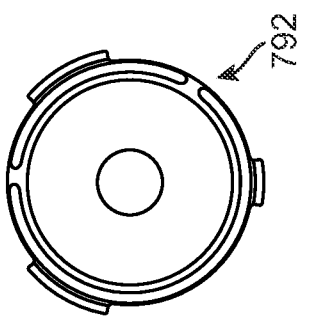
Figure 58:
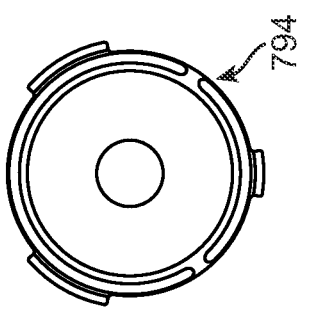
Figure 59:
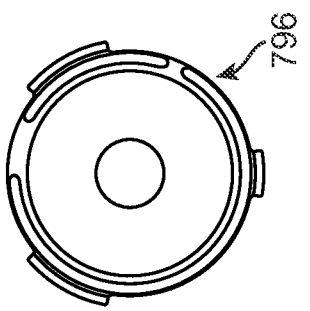
Figure 60:
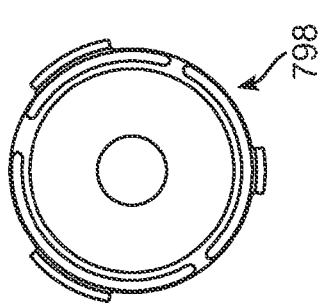
Figure 61:
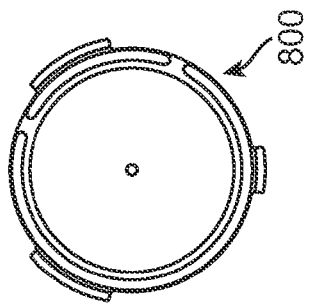
Figure 62:
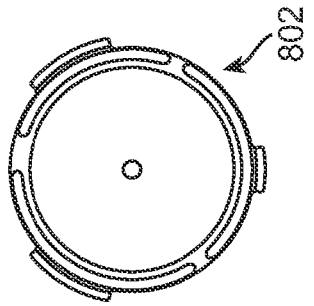
Figure 63:
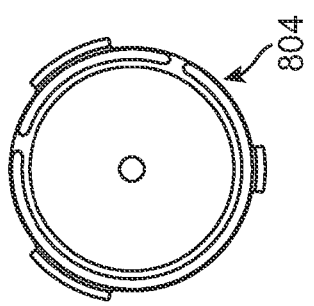
Figure 64:
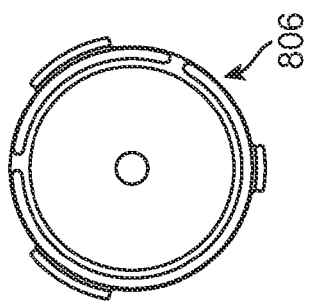
Figure 65:
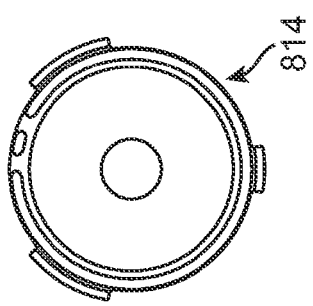
Figure 66:
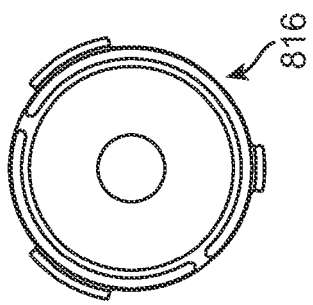
Figure 67:
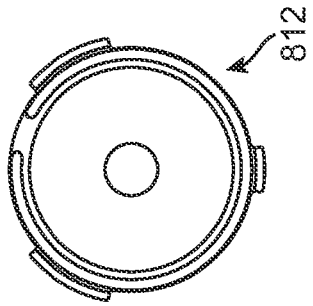
Figure 68:
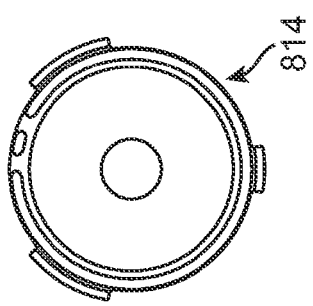

FIG. 10 illustrates the conical collimator 400 in accordance with some embodiments. The conical collimator 400 includes a cylinder (tubular structure) 600 having a first end 602 and a second end 604. The first end 602 is coupled to a head 620 with an opening 622 configured to receive radiation, and allow the radiation to pass therethrough. The second end 604 of the tubular structure 600 has a corresponding opening 624 that aligns with the opening 622. The tubular structure 600 contains a material which functions as a collimating portion for blocking radiation that is transmitted towards the head 620. Part of the radiation is allowed to exit through the opening 624 at the second end 604 of the conical collimator 400.

As shown in the figure, the head 620 of the conical collimator 400 includes an interface surface 630 having a plurality of indentations 632 (e.g., grooves). The indentations 632 on the interface surface 630 define one or more engaging portions 640 configured to engage with one or more of the switches 360 at the interface device 344. As shown in the figure, there are three indentations 632a-632c that collectively define two engaging portions 640a, 640b. In other embodiments, the conical collimator 400 may include other number of indentations 632 and other number of engaging portions 640. Each engaging portions 640 may be configured to engage with one of the switches 360, or alternatively, a plurality of switches 360 (depending on how far apart the indentations 632 are apart from each other). The activation of each switch 360 creates a signal that form a code or a part of a code. Thus, the indentations 632 on the conical collimator 400 provide a code that may be used to determine the identity of the conical collimator 400.

The head 620 of the conical collimator 400 also includes protrusions 660a-660c located circumferentially at the side 670 of the head 620. The protrusions 660a-660c are configured to mate with the respective openings 522a-522c at the coupling device 340. In particular, during use, the protrusions 660a-660c of the conical collimator 400 are placed through the respective openings 522a-522c at the coupling device 340. The conical collimator 400 is then turned relative to the coupling device 340 to place the protrusions 660a-660c underneath the three locking portions 524a-524c of the secure ring 520, thereby locking the conical collimator 400 relative to the interface device 344 of the mounting device 340.

The conical collimator 400 also includes a marking 674 for indicating a size of the opening 622 or a size of the radiation beam that is provided by the conical collimator 400. In the illustrated embodiments, the marking 674 is "10" indicating that the conical collimator 400 is configured to provide a pencil beam having a cross sectional dimension of 10 mm at an isocenter.

In the above embodiments, the conical collimator 400 is described as being used with the mounting device 300. In other embodiments, the conical collimator 400 may be considered as a part of the mounting device 300. Also, in other embodiments, the mounting device 300 and/or the conical collimator 400 may be considered to be part(s) of the radiation system 10.

As discussed, the conical collimator 400 may be configured (e.g., designed and/or built) so that the engaging portions 640 on the interface surface 630 engage with one or more of the switches 360. In particular, the engaging portions 640 of the conical collimator 400 may have different configurations (e.g., different sizes, positions, etc.) in different embodiments. For example, in other embodiments, the conical collimator 400 may have any of the configurations shown in FIGS. 11-69.

Figure 69:
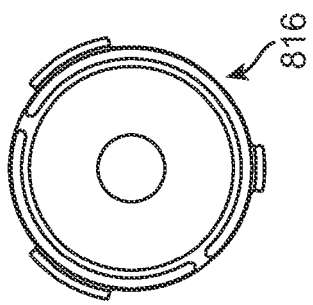

FIGS. 11-69 illustrate a set of conical collimators 700-816 that are configured to provide radiation beams with different respective cross sectional dimensions. The conical collimators 700-816 have the same configuration as that of the conical collimator 400, except that they have different groove patterns 632, different engaging portions 640, and different sizes of the opening 622. In some embodiments, the conical collimators 700-816 provide different respective beam sizes that range from 5 mm to 47.5 mm. In other embodiments, the range of beam sizes provided by the set of conical collimators 700-816 may be different from that described previously. Thus, each of the conical collimators 700-816 is configured to engage with a different subset of the switches 360 at the mounting device 340. In some embodiments, the conical collimators 700-816 are configured to be selectively used with the mounting device 300. In other embodiments, the conical collimators 700-816 may be considered as parts of the mounting device 300. Thus, as used in this specification, the term "device" may refer to one or more apparatus or component(s) that may or may not be coupled together.

In a method of using the mounting device 300, the mounting device 300 is first secured relative to the radiation system 10. Such may be accomplished by sliding portions 304, 306 of the mounting device 300 into the slots 208, 210 of the interface structure 200 of the radiation system 10. When this occurs, the securing mechanisms 322, 324 of the mounting device 300 engage with the pins 212, 214 at the interface structure 200 of the radiation system 10, thereby automatically placing the mounting device 300 at a desired position relative to the interface structure 200, and securing the mounting device 300 relative to the interface structure 200. The securing mechanism 324 can then be operated to move the connector 394 towards the connector 220 at the interface structure 200 so that the connector 394 is electrically coupled to the connector 220.

The pins 502, 504 may then be selectively turned to adjust the position of the base 500 (and therefore, the coupling device 340) relative to the support structure 302 along two respective orthogonal axes. Also, the pins 510a-510d may be selectively turned to tilt the interface device 344 about different axes relative to the support structure 302. After the position and orientation of the interface device 344 have been desirably adjusted, the cover 540 may then be placed over the interface device 344 to prevent accidental operation of the pins 502, 504, 510a-510d.

Next, depending on the particular requirement of a treatment plan, the operator then selects one of the conical collimators 700-816 for use with the mounting device 300. For example, if the particular treatment plan requires that the conical collimator with size No. 8 be used, then the operator selects conical collimator 702 that has the required size. The operator then places the head 620 of the conical collimator into the opening 342 of the interface device 344 (like that shown in FIG. 5).

In the illustrated embodiments, when the head 620 of the conical collimator is placed on top of the surface 368 at the interface device 344, the head 620 presses down the lever 370, thereby causing a signal to be generated at the PCB 390. The signal is then transmitted via the cable 392 and the electrical connector 394 to the connector 220 at the interface structure 200 of the radiation system 10. The signal may then be processed by the processor 54 (or another processor). In the illustrated embodiments, in response to the signal received by the processor 54, the processor 54 determines that the conical collimator 400 is placed at its operative position relative to the interface device 344, and allows the gantry 12 of the radiation system 10 to rotate. In other embodiments, even when the collimator 400 is in place, the processor 54 will not allow the gantry 12 to rotate until a locking ring (described below) is used to lock the collimator 400 against the interface device 344.

After the head 620 of the conical collimator 400 is placed into the opening 342, the secure ring 520 is then used to secure the conical collimator 400 relative to the interface device 344. In particular, the protrusions 660a-660c at the side 670 of the conical collimator 400 are placed through the recesses 522a-522c at the secure ring 520 at the interface device 344, and the conical collimator 400 is turned to place the protrusions 660a-660c underneath the portions 524a-524c of the secure ring 520, thereby securing the conical collimator 400 relative to the interface device 344. When the conical collimator 400 is at its operative position relative to the interface device 344, the surface 630 at the head 620 of the conical collimator 400 faces towards the ring surface 350 of the interface device 344, and the engaging portions 640 at the surface 630 of the conical collimator 400 engage with a subset (e.g., one, some, or all) of the switches 360. The engagement with the subset of switches 360 causes corresponding signals to be generated at the PCB 390, which are then transmitted via the cable 392 and the electrical connector 394 to the electrical connector 220 at the interface structure 200 of the radiation system 10. For example, if the engaging portions 640 activates switches 360b and 360e, then the activated switches 360b, 360e cause corresponding signals to be generated at the PCB 390. In some embodiments, the signals are transmitted to the processor 54 (or another processor) for processing. In the illustrated embodiments, the six switches 360a-360f allow the PCB 390 to read the groove pattern on the base 620 of the conical collimator 400 to form a unique code that is specific for the particular conical collimator 400.

In the illustrated embodiments, the processor is configured to determine the identity of the conical collimator 400 based on the switch signals received from the PCB 390, and compare the identity of the conical collimator 400 against that required by the treatment plan. In one implementation, the processor may be configured to look up a table, which provides an identity of the conical collimator 400 based on the set of switches 360 activated by the conical collimator 400. In the illustrated embodiments, each switch 360 provides a binary value (0 or 1), and therefore, the six switches 360a-360f collectively may uniquely code a total of $2^6$=64 conical collimators 400. In other embodiments, the number of coding switches 360 may be less than six or more than six. Also, in the illustrated embodiments, the seventh switch 360g is a parity switch, which is also set by the groove pattern on the conical collimator 400. The pattern of the seven total switches 360a-360g, as set by the base 620 of the conical collimator 400, is set such that an even number of switches 360 is pressed at any give time. If the number of pressed switches is sensed as odd (including the parity switch), then the system 10 will determine that there is an error, such as a broken switch 360, or an improperly machined conical collimator base 620, or a conical collimator 400 which is not properly inserted or secured in the mount 300.

In some embodiments, if the processor determines that the identity of the conical collimator 400 at the mounting device 300 does not match that required by the treatment plan, then the processor will prevent radiation from being delivered. The processor may also optionally cause an alarm signal be generated to inform the operator that the conical collimator 400 does not match that required by the treatment plan. This has the benefit of preventing mistreatment of the patient due to an incorrectly selected conical collimator 400.

Next, the operator places the locking ring 420 onto the coupling device 340, and screws the locking ring 420 against the threads 424. This causes the locking ring 420 to press the conical collimator against the interface device 344, and further securing the conical collimator relative to the interface device 344. The completed configuration is like that shown in FIG. 6. In the illustrated embodiments, when the locking ring 420 is screwed onto the interface device 344, the locking ring 420 presses the button 380 at the interface device 344. This causes the PCB 390 to generate a signal, which is then transmitted via the cable 392 and the electrical connector 394 to the connector 220 at the interface structure 200 of the radiation system 10. In some embodiments, the signal is processed by the processor 54 (or another processor), which when receives the signal, determines that the locking ring 420 is in place, thereby allowing radiation to be delivered by the radiation system 10. In such cases, the processor 54 will initially allow the gantry 12 to rotate when it determines that the conical collimator 400 is in place based on the pressing of the lever 370, and when the processor 54 later senses that the locking ring 420 is in place, then the processor 54 would allow radiation to be delivered. In other embodiments, the processor 54 would not allow the gantry 12 to rotate even when the lever 370 is actuated. In such cases, the processor 54 will allow both rotation of the gantry 12 and delivery of radiation when it determines that the conical collimator 400 is in place (based on the pressing of the lever 370) and that the locking ring 420 is secured (based on the pressing of the button 380).

As illustrated in the above embodiments, the mounting device 300 and the conical collimator 400 are advantageous because they provide automatic verification of the selected conical collimator 400 against that required by the treatment plan, without requiring human visual inspection, which may not be reliable. In addition, because the mounting device 300 is electrically coupled to the system's 10 interlock logic (which prevents radiation from being delivered when the conical collimator 400 at the mounting device 300 does not match that of the treatment plan), use of the mounting device 300 automatically prevents the wrong conical collimator from being used to mistreat patient. Also, embodiments described herein obviate the need for the operator to manually check the selected conical collimator 400, and provides automatic verification of the selected conical collimator 400 in an accurate and efficient manner. The mounting device 300 and the conical collimator 400 also allow the system 10 to automatically determine that the conical collimator 400 is correctly positioned and secured relative to the mounting device 300, without requiring the operator to perform any manual inspection (which again, may be unreliable).

In other embodiments, instead of using machined feature(s) to code the conical collimator 400, resistors of a specific resistance may be inserted into/onto the head 620 of the conical collimator 400, which may be detected and processed by electronics inside the mounting device 300. In such cases, instead of using mechanically actuated switches 360, the mounting device 300 may include sensors for sensing the resistance of the resistors. However, coding conical collimator 400 using machined feature(s) is more advantageous than the resistors. This is because the range of resistors that may be used with the radiation system 10 may be limited. Also, the electrical contacts between the resistor at the conical collimator 400 and the reader at the mounting device 300 may not be reliable, and may create durability problem over repeated use.

Computer System Architecture

Figure 70:
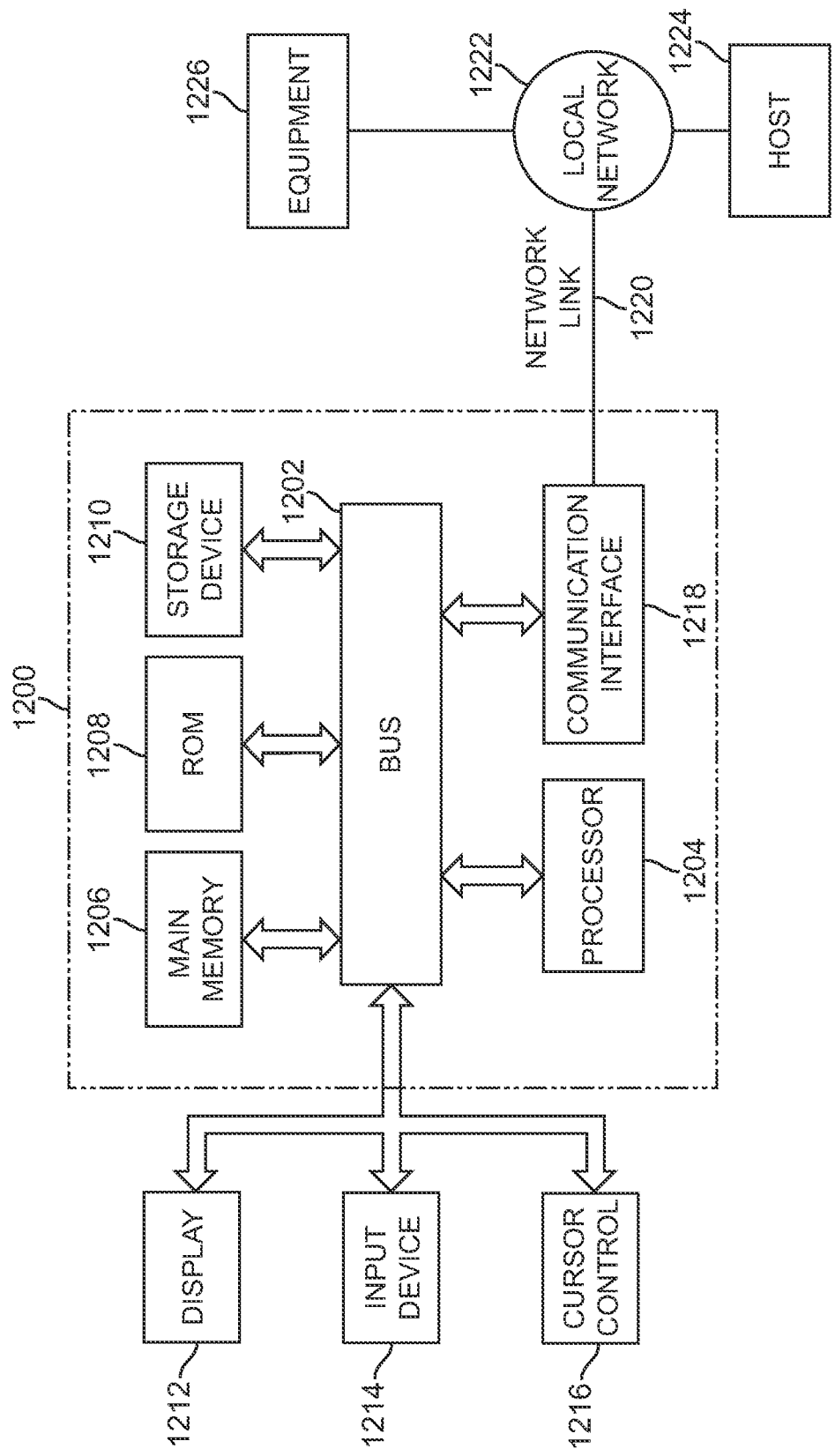
FIG. 70 is a block diagram of a computer system architecture, with which embodiments described herein may be implemented.

FIG. 70 is a block diagram that illustrates an embodiment of a computer system 1200 upon which an embodiment of the invention may be implemented. Computer system 1200 includes a bus 1202 or other communication mechanism for communicating information, and a processor 1204 coupled with the bus 1202 for processing information. The processor 1204 may be an example of the processor 54 of FIG. 1, or another processor that is used to perform various functions described herein. In some cases, the computer system 1200 may be used to implement the processor 54. The computer system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The computer system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The computer system 1200 may be coupled via the bus 1202 to a display 1212, such as a cathode ray tube (CRT), for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The computer system 1200 may be used for performing various functions (e.g., calculation) in accordance with the embodiments described herein. According to one embodiment, such use is provided by computer system 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process steps described herein. One or more processors in a multi-processing arrangement may also be employed to execute the sequences of instructions contained in the main memory 1206. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1204 for execution. Such a medium may take many forms, including but not limited to, non-volatile media, volatile media, and transmission media. Non-volatile media includes, for example, optical or magnetic disks, such as the storage device 1210. A non-volatile medium is an example of a non-transitory medium. Volatile media includes dynamic memory, such as the main memory 1206. A volatile medium is another example of a non-transitory medium. Transmission media includes coaxial cables, copper wire and fiber optics, including the wires that comprise the bus 1202. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the computer system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The computer system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the computer system 1200, are exemplary forms of carrier waves transporting the information. The computer system 1200 can send messages and receive data, including program code, through the network (s), the network link 1220, and the communication interface 1218.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A device for use with a radiation machine, comprising:
   a structure for mounting to the radiation machine;
   a coupling device coupled to the structure, the coupling device having an opening for accommodating a portion of a first cone collimator; and
   a plurality of movable switches at the coupling device, wherein one or more of the plurality of switches are configured to be actuated in response to the portion of the first cone collimator being placed in the opening;
   wherein each of the plurality of switches comprises a surface that is moveable relative to the coupling device.

2. The device of claim 1, wherein the surface comprises a curvilinear surface.

3. The device of claim 1, further comprising a printed circuit board to which the plurality of switches is coupled.

4. The device of claim 3, wherein the printed circuit board is configured to determine if the portion of the first cone collimator is placed in the opening.

5. The device of claim 3, wherein the printed circuit board is configured to determine an identity of the first cone collimator based on the one or more of the plurality switches that are actuated.

6. The device of claim 1, further comprising the first cone collimator, wherein the first cone collimator has one or more engaging portions that are configured to engage with the one or more of the plurality of switches.

7. The device of claim 6, further comprising a second cone collimator having a different configuration from that of the first cone collimator.

8. The device of claim 7, wherein the one or more engaging portions of the first cone collimator are configured to engage with a first subset of the plurality of switches that includes the one or more of the plurality of switches, and the second cone collimator is configured to engage with a second subset of the plurality of switches that is different from the first subset.

9. The device of claim 1, further comprising a lever configured to be automatically actuated when the portion of the first cone collimator is placed in the opening, wherein the lever is coupled to a circuitry for generating a signal for indicating that the first cone collimator is placed in the opening.

10. The device of claim 1, wherein the coupling device is moveably mounted to the structure.

11. A device for use with a radiation machine, comprising:
    a structure for mounting to the radiation machine;
    a coupling device coupled to the structure, the coupling device having an opening for accommodating a portion of a first cone collimator;
    a plurality of movable switches at the coupling device, wherein one or more of the plurality of switches are configured to be actuated in response to the portion of the first cone collimator being placed in the opening; and
    a locking ring for locking the first cone collimator against the coupling device, wherein the locking ring is configured to detachably couple to the coupling device.

12. The device of claim 11, wherein the locking ring comprises a first ring structure, and a second ring structure that is moveably coupled to the first ring structure.

13. The device of claim 11, further comprising a button at the structure or at the coupling device that is actuatable by the locking ring when the locking ring is detachably coupled to the coupling device, wherein the button is coupled to a first circuitry for generating a first signal for indicating that the locking ring is detachably coupled to the coupling device.

14. The device of claim 13, further comprising a lever configured to be automatically actuated when the portion of the cone collimator is placed in the opening, wherein the lever is coupled to a second circuitry for generating a second signal for indicating that the cone collimator is placed in the opening.

15. The device of claim 14, further comprising a third circuitry for processing one or both of the first and second signals, and for controlling an operation of the radiation machine.

16. The device of claim 15, wherein the third circuitry is configured to allow a gantry of the radiation machine to move in response to the second signal, and allow a source of the radiation machine to deliver radiation in response to both the first and second signals.

17. A device for use with a radiation machine, comprising:
    a first cone collimator, wherein the first cone collimator has a first end for receiving a radiation beam, a collimating portion for changing the radiation beam, and a second end for emitting an output beam;
    wherein the first cone collimator is configured to be detachably coupled to a coupling device that has a plurality of moveable switches, and has one or more engaging portions configured to engage with a first subset of the plurality of switches, each of the plurality of switches having a surface that is moveable relative to the coupling device.

18. The device of claim 17, wherein the one or more engaging portions of the first cone collimator are configured to allow identification of the first cone collimator by a processor.

19. The device of claim 17, further comprising a second cone collimator having a different configuration from that of the first cone collimator.

20. The device of claim 19, wherein the second cone collimator is configured to engage with a second subset of the plurality of switches that is different from the first subset.

21. The device of claim 19, wherein the first cone collimator has a first opening for emitting the output beam, the second cone collimator has a second opening for emitting another output beam, wherein the first opening and the second opening have different respective sizes.

22. The device of claim 17, wherein the surface comprises a curvilinear surface.

23. The device of claim 22, further comprising a printed circuit board to which the plurality of switches is coupled.

24. The device of claim 23, wherein the printed circuit board is configured to determine if a portion of the first cone collimator is placed in an opening of the coupling device.

25. The device of claim 23, wherein the printed circuit board is configured to determine an identity of the first cone collimator based on the first subset of the plurality switches that are engaged by the one or more engaging portions of the first cone collimator.

26. A device for use with a radiation machine, comprising:
a structure for mounting to the radiation machine;
a coupling device coupled to the structure, the coupling device having an opening for accommodating a portion of a first cone collimator; and
a plurality of movable switches at the coupling device, wherein one or more of the plurality of switches are configured to be actuated in response to the portion of the first cone collimator being placed in the opening;
wherein the plurality of switches comprises at least six switches.

27. A device for use with a radiation machine, comprising:
a structure for mounting to the radiation machine;
a coupling device coupled to the structure, the coupling device having an opening for accommodating a portion of a first cone collimator;
a plurality of movable switches at the coupling device, wherein one or more of the plurality of switches are configured to be actuated in response to the portion of the first cone collimator being placed in the opening; and
a first screw for moving the coupling device relative to the structure in a first direction, and a second screw for moving the coupling device relative to the structure in a second direction;
wherein the coupling device is moveably mounted to the structure.

28. A device for use with a radiation machine, comprising:
a structure for mounting to the radiation machine;
a coupling device coupled to the structure, the coupling device having an opening for accommodating a portion of a first cone collimator;
a plurality of movable switches at the coupling device, wherein one or more of the plurality of switches are configured to be actuated in response to the portion of the first cone collimator being placed in the opening; and
a plurality of adjustors for tilting the coupling device relative to the structure about at least two axes;
wherein the coupling device is moveably mounted to the structure.

* * * * *